(12) United States Patent
Kollmeyer et al.

(10) Patent No.: US 8,960,193 B2
(45) Date of Patent: Feb. 24, 2015

(54) MOBILE MEDICAL VENTILATOR

(75) Inventors: Phillip J. Kollmeyer, Fond du Lac, WI (US); Stefan I. Kutko, New York, NY (US); Robert Tham, Middleton, WI (US); Norman Rick, Mt. Horeb, WI (US); Jonathan L. Woods, Madison, WI (US)

(73) Assignee: General Electric Company, Schenectady, NY (US)

( * ) Notice: Subject to any disclaimer, the term of this patent is extended or adjusted under 35 U.S.C. 154(b) by 2135 days.

(21) Appl. No.: 11/707,379

(22) Filed: Feb. 16, 2007

(65) Prior Publication Data

US 2008/0196720 A1    Aug. 21, 2008

(51) Int. Cl.
| A61M 16/08 | (2006.01) |
| A61M 16/00 | (2006.01) |
| A62B 7/00 | (2006.01) |

(52) U.S. Cl.
CPC ........... *A61M 16/00* (2013.01); *A61M 16/0081* (2014.02); *A61M 16/0057* (2013.01); *A61M 16/0075* (2013.01); *A61M 2016/0027* (2013.01); *A61M 2016/0039* (2013.01); *A61M 2205/42* (2013.01)
USPC ............. 128/205.13; 128/204.21; 128/204.18

(58) Field of Classification Search
CPC ...................... A61M 16/0075; A61M 16/0057; A61M 16/0096; A61M 16/01; A61M 16/08; A61M 16/10; A61M 16/104
USPC .............. 128/204.18, 204.21, 205.13, 205.14
See application file for complete search history.

(56) References Cited

U.S. PATENT DOCUMENTS

| 3,675,649 | A |   | 7/1972  | Basham et al. |
| 4,484,578 | A |   | 11/1984 | Durkan |
| 4,587,967 | A |   | 5/1986  | Chu et al. |
| 4,796,467 | A |   | 1/1989  | Burt et al. |
| 4,941,469 | A | * | 7/1990  | Adahan .................... 128/205.18 |
| 4,958,636 | A |   | 9/1990  | Blandino et al. |
| 5,106,268 | A |   | 4/1992  | Kawamura et al. |
| 5,315,989 | A |   | 5/1994  | Tobia |
| 5,555,880 | A |   | 9/1996  | Winter et al. |
| 5,647,352 | A | * | 7/1997  | Niemi et al. ............. 128/204.28 |
| 5,651,360 | A |   | 7/1997  | Tobia |
| 5,673,688 | A | * | 10/1997 | Tham et al. .............. 128/204.22 |
| 5,735,267 | A | * | 4/1998  | Tobia ....................... 128/204.21 |
| 5,823,186 | A |   | 10/1998 | Rossen et al. |

(Continued)

OTHER PUBLICATIONS

U.S. Appl. No. 11/461,792, filed Aug. 2, 2006 Entitled "Pressure Targeted Ventilator Using an Oscillating Pump" Applicants: Phillip Kollmeyer et al.

*Primary Examiner* — Valerie L Skorupa

(74) *Attorney, Agent, or Firm* — Andrus Intellectual Property Law, LLP

(57) ABSTRACT

A ventilatory system for providing ventilatory support to a patient without the need for an external source of pressurized drive gas. The ventilatory system comprises a drive pump and a controller such that the drive pump collects ambient air and may pressurize it to a pressure determined by the controller. The controller may signal to the drive pump to pressurize the collected ambient air to a first pressure for delivering ventilatory support to a patient and a second pressure for providing PEEP support to a patient. The controller may signal to the drive pump to deliver a targeted flow and/or volume of collected ambient air to the bellows to provide volumetric ventilatory support during inhalation and a PEEP support during exhalation.

18 Claims, 6 Drawing Sheets

(56) References Cited

U.S. PATENT DOCUMENTS

| | | |
|---|---|---|
| 5,871,008 A | 2/1999 | Poon et al. |
| 5,957,129 A * | 9/1999 | Tham et al. .............. 128/204.28 |
| 6,071,087 A | 6/2000 | Jalink, Jr. et al. |
| 6,085,746 A * | 7/2000 | Fox .......................... 128/204.19 |
| 6,257,234 B1 | 7/2001 | Sun |
| 6,279,574 B1 | 8/2001 | Richardson et al. |
| 6,289,890 B1 * | 9/2001 | Bliss et al. ............... 128/203.11 |
| 6,349,723 B1 * | 2/2002 | Kock ....................... 128/203.28 |
| 6,371,113 B1 * | 4/2002 | Tobia et al. .............. 128/204.23 |
| 6,390,091 B1 * | 5/2002 | Banner et al. ............ 128/204.21 |
| 6,644,310 B1 | 11/2003 | Delache et al. |
| 6,651,658 B1 * | 11/2003 | Hill et al. ................. 128/204.23 |
| 2001/0009152 A1 | 7/2001 | Bennarsten |
| 2006/0021620 A1 * | 2/2006 | Calluaud et al. ......... 128/204.22 |
| 2006/0091160 A1 | 5/2006 | Sweeton |
| 2006/0157058 A1 | 7/2006 | Aylsworth et al. |
| 2007/0248474 A1 | 10/2007 | Dietzsch et al. |
| 2008/0029096 A1 * | 2/2008 | Kollmeyer et al. ...... 128/204.21 |

* cited by examiner

MOBILE MEDICAL VENTILATOR

FIELD OF THE DISCLOSURE

The disclosure is directed towards mechanical ventilators for providing a patient with respiratory support including the delivery of anesthesia as well as ventilatory support. Specifically, the disclosure is directed towards a mechanical ventilator with increased mobility.

BACKGROUND OF THE DISCLOSURE

Patients that have respiratory difficulties often must be placed on a mechanical ventilator. These respiratory difficulties may be pathological in nature or may be due to the fact that the patient is too weak or sedated to independently perform respiration functions. Often, the patient may be spontaneously attempting to breathe but is not able to complete a full respiratory cycle. In these cases, mechanically assisted ventilation is provided. In some mechanically assisted ventilation platforms, a combination of pressure and/or flow sensors detect a patient's breath attempt. Detection of a breath attempt triggers the mechanical delivery of a breath. The breath is provided by the delivery of medical gases under a pressure that is sufficient to overcome the system resistance and the patient's airway resistance to fill the lungs in an inspiratory phase. When the pressure of the medical gas is reduced, the natural elasticity of the patient's chest wall forces the delivered breath out of the patient in an expiratory phase.

The medical gases supplied to the patient may comprise air, oxygen, helium, nitric oxide, anesthetic agent, drug aerosol, or any other gas breathed by the patient. Air is referred to as the drive gas for the ventilator system and any other medical gases are referred to as supplemental gases to the air.

The healthcare industry faces the challenge of providing higher quality care, while reducing the cost of providing that care. One aspect of the challenge to reduce cost is to reduce the fundamental costs that are associated with the provision of healthcare. Fundamental costs are the costs that are associated with the infrastructure needed to provide medical care to patients, for example, the costs of medical gas used to provide ventilatory support. Additionally, a need exists for an improved quality of care provided in remote locations such as military field hospitals, third world countries, and rescue or emergency situations. One aspect that is common to meeting these challenges is to provide equipment that is mobile. The mobility of a piece of equipment includes reducing the equipment's need for external components, such as tanks of medical gas, or an external medical gas supply. The increased mobility of a piece of equipment allows for it to be moved around a hospital to the area where it is currently needed and allows for a piece of equipment to be transported to a remote location where other less portable equipment is not available.

There are currently a wide variety of systems available to provide ventilatory support to a patient, or to provide anesthesia delivery to a patient. There are systems that combine both of these functionalities, as disclosed in U.S. Pat. No. 5,315,989, which is incorporated in its entirety herein; however, these systems require a supply of pressurized medical gas in order to provide the respiratory support to the patient. Medical gas is often supplied from pressurized supply tanks, or medical gas may be delivered to the ventilator via gas connections in the wall of a room in the hospital. Dependence upon fixed-location gas connections severely limits the portability of a ventilatory system as the system can only be used in those rooms that have been outfitted with medical gas supply lines, tapping into a centralized supply of medical gas. Furthermore, dependence upon medical gas supply lines increases the cost of adding additional rooms to a hospital facility since each of these new rooms must be connected to the centralized supply of medical gas and outfitted with the medical gas supply lines. Alternatively, smaller and thus more portable medical gas supply tanks may be used by an individual ventilatory system. However, these tanks are more expensive and, while mobile, are still cumbersome to transport.

A third type of ventilatory system currently available reduces the need for a supply of medical gas, where the medical gas to be used is air, by integrating a pump with the ventilatory system such that the pump pressurizes the ambient air to the pressure required by the ventilatory system. Ventilatory systems integrated with a high pressure pump for pressurizing ambient air suffer from limitations inherent with high pressure pumps. In general, high pressure pumps suffer from the fact that they are relatively large and heavy which thus reduces the portability of systems using these pumps. The weight of the pump is counter-productive as the implementation of a ventilatory system with a pump is generally for the purpose of making the ventilatory system a mobile one. Alternatively, non-high pressure pump systems (e.g., blower or turbine systems) generally have a slow response time for delivering the proper supply of medical gas to the patient at the proper time. To compensate for this, non-high pressure pump systems are used with complicated valves and circuitry, thus increasing the amount of power used to operate the ventilator system. This too is not desirable in a mobile ventilatory support system.

Therefore, a patient respiratory support system that can provide sufficient medical gas pressure to ensure proper patient ventilation, provide a fast response time to continually adjust the pressure delivered in conjunction with the patient's respiratory cycle, provide low power consumption, and reduced system size and weight is desirable. A patient's respiratory support system that uses a pump that combines these qualities would greatly increase the mobility of a patient respiratory support system, thus allowing greater flexibility in the locations where the patient may receive respiratory support.

SUMMARY OF THE DISCLOSURE

Embodiments provide a patient respiratory support system that is mobile, has a fast response time, and conserves electrical power when compared to high pressure compressor pump systems. The patient respiratory support system of the present invention utilizes a drive pump to control the delivery of the medical gas to the patient. The drive pump provides a dependable source of high flow rate and energy efficient drive gas supply for the ventilatory system of the present invention. Thus, a ventilatory system comprising a drive pump provides a solution to hospitals with budgetary needs due to the fact that the drive pump can provide the needed pressurized medical gas to a ventilatory system capable of providing either ventilatory support or anesthesia delivery support to a patient. Because of the mobile nature of the present invention, the present invention may be moved about the medical facility to provide respiratory support to a patient that needs it, thus increasing the scalability of a brick and mortar medical care facility.

A further embodiment, utilizes an oscillating pump as the drive pump for producing a flow of ambient air.

In another embodiment, the drive pump is capable of pressurizing the ventilatory system to provide positive end expiratory pressure (PEEP) support.

In a still further embodiment, the ventilatory system comprises a sound dampening device to reduce the noise exterior to the drive pump.

BRIEF DESCRIPTION OF THE DRAWINGS

The drawings illustrate the best mode presently contemplated of carrying out the invention. In the drawings.

DETAILED DESCRIPTION

Figure 1:
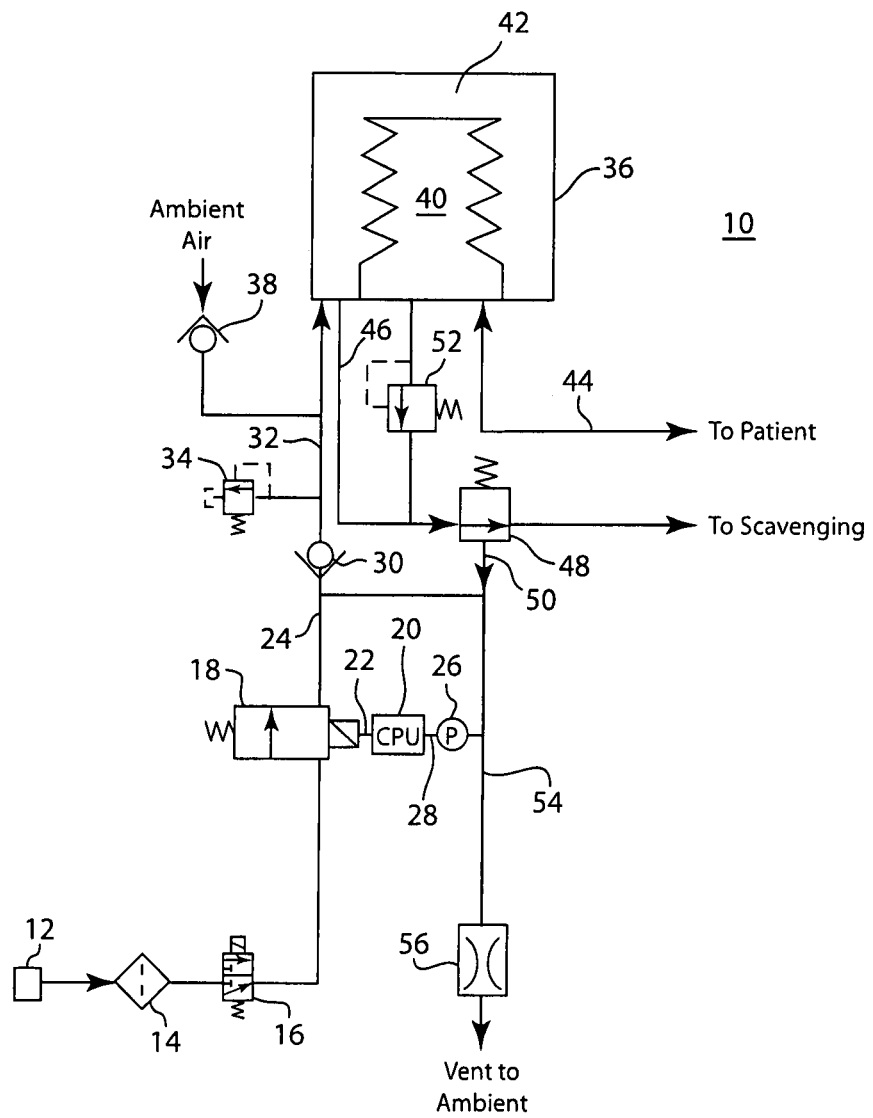
FIG. 1 is a schematic diagram of the pneumatic system of a prior art ventilatory system.

FIG. 1 depicts a schematic diagram of a ventilatory system 10 known in the art. A ventilator of this system is described in U.S. Pat. No. 5,315,989 to Tobia, which is herein incorporated in its entirety by reference. In ventilatory system 10, a pressurized source of medical gas 12 is connected to a regulator 14 and a gas inlet valve 16. The pressurized medical gas serves as the drive gas for operating the ventilatory system 10. The pressurized gas flows from the inlet valve 16 to an inspiratory flow control valve 18. Typically, the inspiratory flow control valve 18 is a proportional flow solenoid valve, but many other suitable types of valves exist, including single or multiple pulse-width modulated (PWM) two-position valves. The inspiratory flow control valve 18 is controlled by CPU 20 via line 22. The CPU 20 directs the inspiratory flow control valve 18 to open and close according to the pressure that is desired to be in a first inspiratory conduit 24. The pressure in inspiratory conduit 24 is measured by manifold pressure sensor 26 which sends a pressure signal via line 28 back to the CPU 20.

Inspiratory flow control valve 18 opens and closes upon direction by CPU 20 such that the constant supply of pressurized medical gas from the gas source 12 is controlled to produce varying pressures within the first inspiratory conduit 24. Medical gas in the first inspiratory conduit 24 flows through a check valve 30 into conduit 32. Check valve 30 typically requires a threshold pressure in inspiratory conduit 24 in order to open, allowing medical gas to flow into the second inspiratory conduit 32. In an embodiment, the check valve 30 may require pressure greater than 3.5 cmH$_2$O in the first inspiratory conduit 24. Second inspiratory conduit 32 further comprises a mechanical overpressure valve 34. The mechanical overpressure valve 34 maintains safety of the patient receiving mechanical ventilation by venting any excess pressure in and above a threshold amount, typically about 110 cmH$_2$O within the second inspiratory conduit 32 and venting it to the ambient air. Thus, the pressure in the second inspiratory conduit 32 is maintained at a pressure safe for the patient.

The drive gas in second inspiratory conduit 32 is directed to bellows chamber 42 of the bellows assembly 36. The drive gas pressurizes the bellows chamber 42 and compresses the bellows 40. A free breathing check valve 38 is also disposed within the second inspiratory conduit 32. If the patient receiving mechanical ventilation begins to spontaneously breathe the bellows assembly 36 must have a source of gas to deflate the bellows 40 independently of the drive gas. Therefore, the presence of a negative pressure in the bellows 40 relative to the pressure in the bellows chamber 42 will result in the opening of the free breathing check valve 38 such that ambient air is drawn into the second inspiratory conduit 32 and directed to bellows chamber 42 such that the bellows 40 may be compressed and the patient can take a spontaneous breath. The compression of the bellows 40 directs the gas within the bellows 40 to a conduit 44. The conduit 44 is disposed for connection to a patient interface (not depicted) that delivers the medical gas to the patient. The drive gas in the bellows chamber 42 is released through expiratory conduit 46 to an exhalation valve 48. The exhalation valve 48 controls any positive end expiratory pressure (PEEP) that is to be provided to the patient.

PEEP is a type of ventilatory therapy wherein upon patient exhalation, the patient's airway is not returned to the ambient pressure, but instead is held at a pressure above ambient that is determined by the clinician. The PEEP pressure serves to keep the patient's lungs partially inflated and open thereby reducing the patient's airway resistance, increasing lung compliance, and preventing alveolar collapse, or atelectasis. The effect is akin to a rubber balloon which is easier to inflate once it is started by a small inflationary pressure. Keeping the patient lungs partially inflated at the end of expiration also results in the exposure of more of the delivered medical gas to the alveoli that perform the gas exchange within the patient's lungs, thus making the gas exchange more efficient and the ventilation of the patient more effective.

A system for providing PEEP control for a ventilatory system is described in U.S. Pat. No. 5,651,360 to Tobia, which is herein incorporated in its entirety by reference. During exhalation, the exhalation valve 48 controls the pressure of the air in the bellows and correspondingly the pressure of the air in the patient's lungs. The pressure in pressure control conduit 50 controls the pressure restriction provided by the pneumatic exhalation valve 48. Pressure control conduit 50 is pressurized to the same pressure as first inspiratory conduit 24 as the pressure control conduit 50 and the first inspiratory conduit 24 are fluidly connected. During exhalation, check valve 30 is sealed because pressure in the bellows chamber 42 plus the bias pressure required to open the check valve 30 is greater than the pressure in the inspiratory conduit 24. The flow therefore bleeds out of bleed resistor 56. Increased pressure in the inspiratory conduit 24, and correspondingly in pressure control conduit 50 results in a greater PEEP pressure in the bellows 40 and the patient's lungs. This has the effect of allowing PEEP control from the control of the inspiratory flow control valve 18. Typically, CPU 20 will vary the opening of the inspiratory flow control valve 18 between a first inspiratory flow and a second expiratory PEEP flow.

A pop-off valve 52 is connected to the bellows 40 such that if the pressure generated during patient exhalation exceeds that of the combination pop-off valve 52 and the pressure conduit 46, the valve opens such that a portion of the gas from bellows 40 will be diverted to the exhalation valve 48. Exhalation valve 48 directs any gas from the pop-off valve 52 and the drive gas in expiratory conduit 46 to a scavenging unit. The scavenging unit removes any medical gases that may be harmful to the clinicians or others in the room with the patient if these gases were allowed to exhaust into the room. If concentrations of some medical gases are allowed to build up on the room, clinicians may be harmed in the form of liver sclerosis or other health effects. The scavenging unit normally vents the medical gases out of the hospital or care facility and exhausts it outside where it will be diluted to non-harmful concentrations in the environment.

Figure 2:
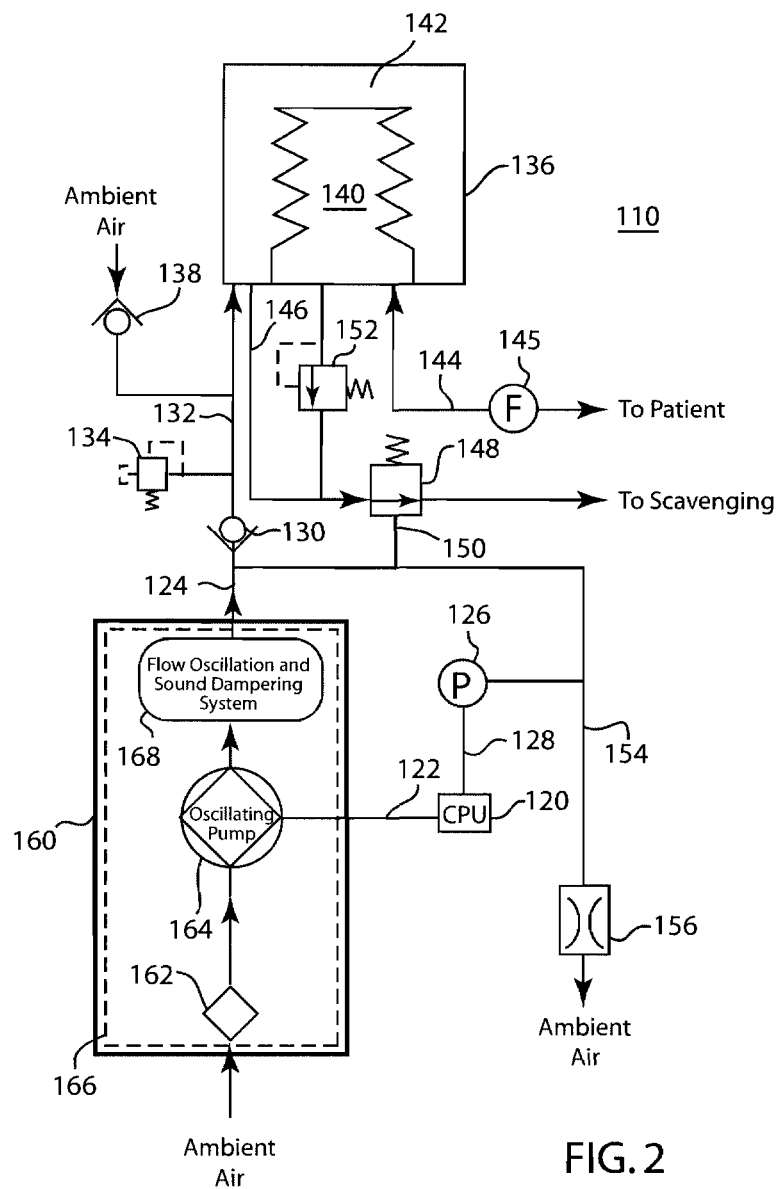
FIG. 2 is a schematic diagram of the pneumatic system of an embodiment.

FIG. 2, is a schematic diagram of an embodiment of a ventilatory system 110 wherein much of the schematic diagram performs similar functions as the prior art described in FIG. 1. Common or unchanged elements from FIG. 1 are depicted in FIG. 2 with a similar one hundred's (100's) level reference number.

A drive pump 160 takes in ambient air and drives a flow of the ambient air into a first inspiratory conduit 124, causing the pressure in the first inspiratory conduit 124 to increase such that the ambient air can be used as the drive gas for the ventilatory system 110. CPU 120 measures the pressure in the first inspiratory conduit 124 via the pressure sensor 126 and controls the drive pump 160 to achieve a specified pressure in the first inspiratory conduit 124. It is understood that the CPU 120 may comprise a variety of elements capable of performing control operations of the ventilatory system 110. In embodiments, CPU 120 may comprise one or more microprocessors or microcontrollers capable of performing parallel processing, or a desktop or laptop personal computer. The CPU 120 receives input from pressure sensor 126 via line 128 as well as other sources of patient ventilatory input (not pictured). The other ventilatory inputs processed by the CPU 120 may include, but shall not be limited to, measured pressures within conduits of the ventilatory system 110, patient airway pressures and gas flows, clinician input data such as respiration rates, I:E ratio, the addition of supplemental gases into the medical gas delivered to the patient. Ventilatory inputs such as those previously described as well as others may be used by CPU 120 in adjusting the controls of the ventilatory system 110.

The CPU 120 directs the drive pump 160 to deliver a commanded flow into inspiratory conduit 124 causing the pressure of the air in the inspiratory conduit 124 to rise to a desired pressure. Thus, the need for a separate pressurized gas source 12, gas regulator 14, gas inlet valve 16, as well as the inspiratory flow control valve 18 as depicted in FIG. 1, is eliminated by the use of the drive pump 160. By eliminating the need for these elements from the prior art, the drive pump 160 increases the mobility of the ventilatory system 110.

Once the ambient air enters the drive pump 160 through an intake filter 162 it is directed to an oscillating pump 164. The oscillating pump 164 receives, from CPU 120, a power signal indicative of the pump flow to drive the pressure in the inspiratory conduit 124 to the desired level. A suitable oscillating pump 164 that may be used is the one disclosed in pending patent application Ser. No. 11/461,792, the complete disclosure of which is herein incorporated by reference. The oscillating pump 164 is advantageous for implementation in this embodiment as the oscillating pump presents the advantages of having a fast response time such that precise control of the pressure of the drive gas can be achieved. It is understood, however, that any suitable drive pump that exhibits a fast response time could be used in the place of the oscillating pump 164. In a further embodiment, oscillating pump 164 is a linear oscillating pump comprising two diaphragms such that a plug of gas is pressurized at each stroke of the linear oscillating pump. A linear oscillating pump may deliver a continuous gas flow. Furthermore, the linear oscillating pump may generate compressed gas flow without frictional mechanical moving parts which reduces wear. It is further understood that other oscillating, piston, or rotary pumps may be used in place of the oscillating pump 164 herein described.

A sound isolation enclosure 166 surrounds the oscillating pump 164 to—attenuate the noise and vibration that is created by the operation of the oscillating pump 164 in the ventilatory system 110. In a clinical setting, excessive noise is undesirable as clear communication between clinician, patients, and patient monitoring systems is desirable for providing quality health care. While the sound isolation enclosure 166 would necessarily need to surround the drive pump 164, embodiments of the present invention may comprise a sound isolation enclosure 166 that also surrounds the intake filter 162 and/or the damping system 168, as depicted. However, in an embodiment comprising a drive pump 160 that does not generate excessive noise, the sound isolation enclosure 166 may not be needed. Finally, the flow of air from the oscillating pump 164 is sent to a damping system 168. The damping system 168 directs the flow of air through a series of baffles (not depicted) to reduce or eliminate the oscillating component of the drive gas flow that is produced as an inherent characteristic of the oscillating pump 164. The damping system 168 further reduces the noise of the pressurized drive gas before it is directed to the inspiratory conduit 124.

The operation of the ventilatory system 110 as depicted in FIG. 2 is now herein described. A patient is receiving mechanical ventilation via ventilatory system 110. The CPU 120 directs the oscillating pump 164 to take ambient air via intake filter 162. This air will be pressurized within the system to be the drive gas for the system. The oscillating pump 164 produces a flow of air into the first inspiratory conduit 124. The flow of air travels to the first inspiratory conduit 124 through the damping system 168 where a substantial portion of the oscillatory frequency content of the drive gas is removed. Next, the drive gas is directed to the first inspiratory conduit 124 to achieve a first target pressure. Upon achieving a minimum pressure difference between the inspiratory conduit 124 and the bellows chamber 142 to open the check valve 130, the drive gas flow is directed through the check valve 130 into the conduit 132. The check valve 130 may typically require about 3.5 cmH$_2$O of pressure in order to open initially, and also prevents the back flow of drive gas from the second inspiratory conduit 132 back into the first inspiratory conduit 124. The second inspiratory conduit 132 directs the drive gas into the bellows chamber 142 of the bellows assembly 136. The pressure in the first inspiratory conduit 124 is monitored by pressure transducer 126.

A buildup of pressure within the bellows chamber 142 compresses the bellows 140 forcing the medical gas within the bellows 140 into conduit 144. The patient connection conduit 144 directs the medical gas to the patient through a patient interface (not depicted) to provide the patient respiratory support. It is also recognized that the flow rate of medical gas delivered to the patient is equal to the drive gas flow delivered by the pump 164 reduced by losses in gas volume due to gas leakage and compliance of the breathing system. The respiratory support can be in the form of pressure or gas volume generated by controlling the drive gas flow out of the drive pump 160 as directed by the CPU 120. A series of ventilatory components (not pictured) may be disposed along the patient connection conduit 144 to provide further respiratory support to the patient. The ventilatory components may comprise, but are not limited to, supplemental medical gas, a nebulizer, a carbon dioxide absorber canister, or a humidifier.

Upon completion of the inspiratory phase of the mechanical ventilation the ventilator cycles to the expiratory phase. The exhaled breath from the patient is directed back to the bellows 140 through the patient connection conduit 144.

When the ventilator cycles to the expiratory phase, the CPU 120 directs the oscillating pump 164 to produce a lower flow of drive gas thus achieving a second, lower target pressure in the first inspiratory conduit 124, the conduit 132, and the bellows chamber 142. As the expired breath from the patient is directed to the bellows 140, the bellows 140 begins to expand within the bellows assembly. The displaced drive gas from the bellows chamber 142 is directed through an expiratory conduit 146 to an exhalation valve 148.

During exhalation, the check valve 130 is nominally closed and the exhalation valve 148, a pressure control conduit 150, and a pop-off valve 152 control the pressure of the medical gas in the bellows chamber 142 and in the bellows 140. The exhalation valve 148 is connected to a pressure control conduit 150 that is in fluid connection with the first inspiratory conduit 124. Therefore, the pressure in the inspiratory conduit 124 created by the flow generated by the oscillating pump 164 is used to control the pressure in the bellows chamber 142. As such, when the patient is in the expiratory phase, the pressure in the bellows 140 is controlled by the pressure to overcome the pop-off valve 152, the pressure in the first inspiratory conduit 124, and the pressure required to maintain the minimal pressure differential across the check valve 130 to keep the check valve 130 closed. The pressure in the bellows 140 is the PEEP pressure delivered to the patient. As such, the patient's exhalation reaches a pressure equilibrium within the bellows 140 at the PEEP pressure, thus maintaining that airway pressure within the patient's lungs.

Pressure transducer 126 is disposed in fluid connection with the first inspiratory conduit 124 such that it provides a signal indicative of the pressure in first inspiratory conduit 124 to the CPU 120. CPU 120 uses the pressure detected by pressure sensor 126 in a feedback loop to accurately determine the power signal needed to drive the oscillating pump 164 to produce the desired drive gas flow to produce the desired pressure in the first inspiratory conduit 124. To prevent a buildup of excess pressure within the first inspiratory conduit 124, a constant bleed of gas is vented to the ambient air by bleed valve 156.

In another embodiment, one or more flow sensors 145 may be disposed in the gas passage between the bellows 140 and the patient exemplarily in conduit 144, to measure the medical gas flow or volume breathed by the patient. The flow sensor 145 may provide a signal to the CPU 120 in a feedback loop to accurately determine the power signal needed to control the oscillating pump 164 to drive the bellows and deliver the desired volume of medical gases to the patient.

The oscillating pump 164 is advantageous for implementation in this embodiment as the oscillating pump presents the advantages of having a fast response time such that precise control of the pressure of the drive gas can be achieved. It is understood, however, that any suitable drive pump that exhibits a fast response time could be used in the place of the oscillating pump 164. In a further embodiment, oscillating pump 164 is a linear oscillating pump comprising two diaphragms such that a plug of gas is pressurized at each stroke of the linear oscillating pump.

Figure 3:
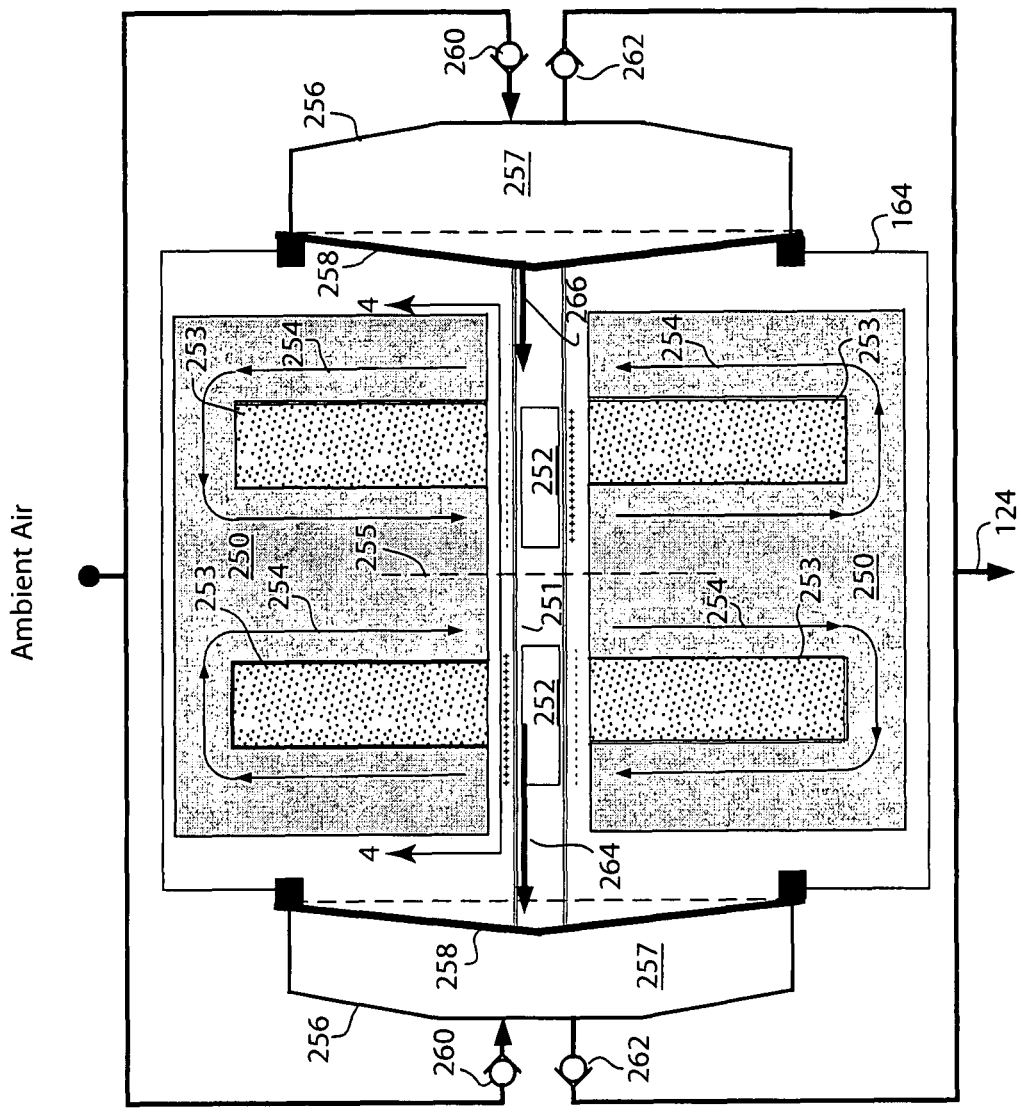
FIG. 3 is an overhead view of the general physical structure of the linear oscillating pump.
Figure 4:
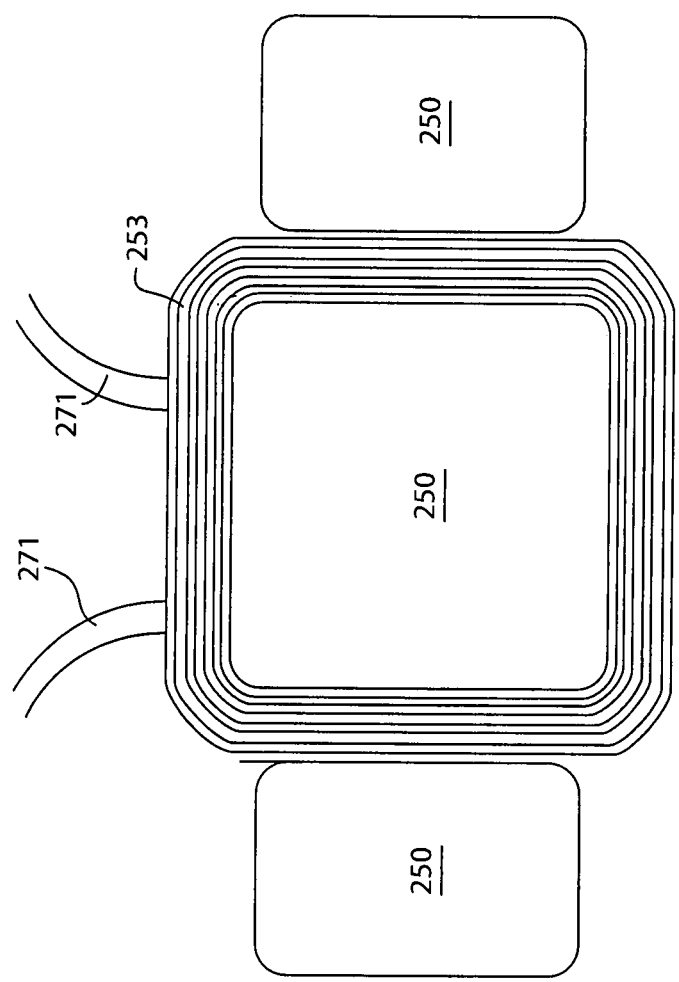
FIG. 4 is a side view of the motor core and windings cut along line 4-4.

FIG. 3 is an overhead view of the general physical structure of an embodiment of the linear oscillating pump 164 as depicted in FIG. 2. As depicted in FIG. 4, which is a cutaway view of the pump along line 4-4, the linear oscillating pump 164 comprises a stator, comprising two annular ferromagnetic laminated motor cores 250 and a plurality of motor windings 253. Referring back to FIG. 3, the pump 164 also comprises a rotor 251. In an embodiment the rotor 251 is a linearly moving rotor 251, however it is understood that it is within the scope of the oscillating pump devices that may produce alternative directions of rotor movement. The rotor 251 comprises two magnets 252, one disposed at either end of the rotor 251.

When an electrical current is applied to the motor windings 253 via leads 271, a magnetic field is produced within the motor cores in the exemplary direction of magnetic field lines 254. These fields push both magnets 252 in the rotor 251 in the same direction, thereby moving one end of the rotor 251 towards the outside of the linear oscillating pump 164 and the other magnet towards the center line 255 of the linear oscillating pump 164.

A pump assembly 256 is disposed on either side of the linear oscillating pump 164 in coaxial relationship to both the motor cores 250 and the magnets 52. Each pump assembly 256 comprises a rubber diaphragm 258, defining a pump chamber 257, an "in" one-way valve 260, and an "out" one-way valve 262.

As the magnetic field 254 through the motor cores 250 forces the rotor 251 towards the outside of the linear oscillating pump 164, this electrical force 264 pushes the rubber diaphragm 258 outwards thereby forcing the air in the pump chamber 257 out through the "out" one-way valve 262 into inspiratory conduit 124. On the other side of the linear oscillating pump 164, the position of rotor 251 proximal to the centerline 255 of the pump 164 produces a mechanical force 266 pulling the rubber diaphragm 258 towards the center of the pump which pulls ambient air through the "in" one-way valve 260 to be stored in the pump chamber 257.

When the direction of current flowing through windings 252 is reversed, the magnetic fields depicted by magnetic field lines 254 reverse forcing the magnets 252 in the opposite direction. As such, the air in the full pump assembly 256 is forced out through the "out" one-way valve 262 and into the inspiratory conduit 124 while the other pump assembly 256 that had been previously emptied now begins to fill with ambient air through the "in" one-way valve 260. This cycle of charges on the motor cores 250 produces the desired output of pressurized gas into the inspiratory conduit 124.

Figure 5:
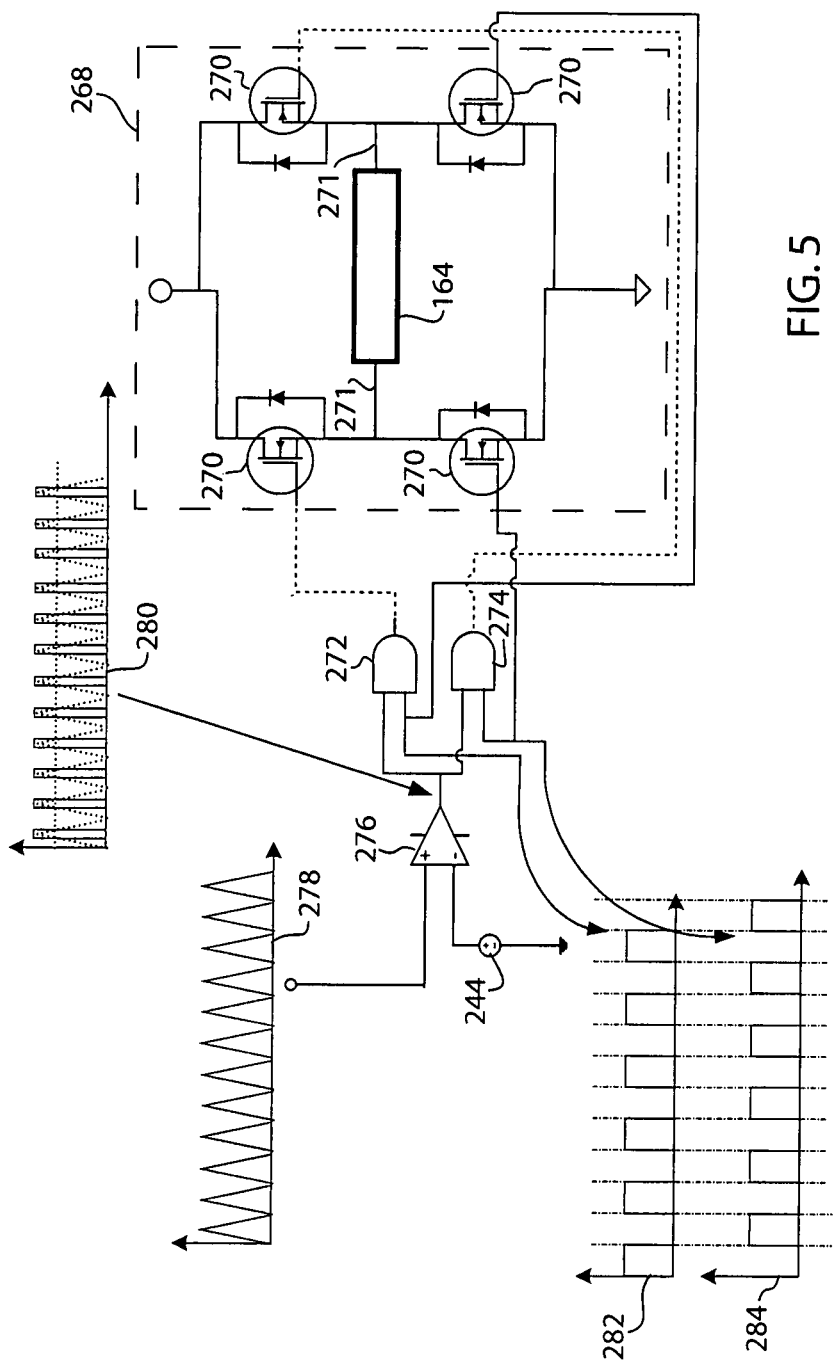
FIG. 5 is a schematic diagram of the electrical signals used to drive the linear oscillating pump.

FIG. 5 depicts a schematic diagram of the electrical signals that are sent via leads 271 to the motor windings 253 of the linear oscillating pump 164. Part or all of which signals may be provided to the linear oscillating pump 164 by CPU 120 via line 122. As an embodiment the motor windings 253 are controlled using an H-bridge inverter 268. It is understood that there are a variety of other DC to AC inversion methods for motor controllers that could be used. The H-bridge inverter 268 comprises four MOSFETs 270. These MOSFETs 270 receive signals from either a first AND gate 272, a second AND gate 274, and from square wave signal 282 or 284. Both the first 272 and second 274 AND gates receive a signal from a comparator 276 which compares a triangular wave 278 with the flow control signal 244 which may be received from the CPU 120. The product from the triangle wave 278 and the flow control signal 244 sent to the comparator 276 produces a comparator signal 280 that is indicative of the desired duty cycle for the operation of the linear oscillating pump 164. A first square wave signal 282 is provided as the second input to the first AND gate 272 and a second square wave signal 284 that is the same frequency as, but 180 degrees out of phase with, the first square wave signal 282 is provided to the second AND gate 274.

In an embodiment, the duty cycle of these two square waves is slightly less than 50% to create a dead time between switching voltage polarity of the pump. The creation of dead time prevents shoot through, the case when two MOSFETs on the same side of the H-Bridge are active and the positive voltage is therefore shorted to ground. First square wave 282 and second square wave 284 operate at a frequency that is equal to that of the motor AC operating frequency. The triangular wave 278 operates at a frequency much greater than the motor operating frequency to implement PWM voltage magnitude control. In an embodiment, the motor drive signal is a 24 V 60 Hz pulse width modified square wave with the effective voltage magnitude of the wave being defined by the output signal 280 of the comparator 276. However, it is understood that any control signal capable of producing an oscillating motion in the oscillating pump may alternatively be used.

Figure 6A:
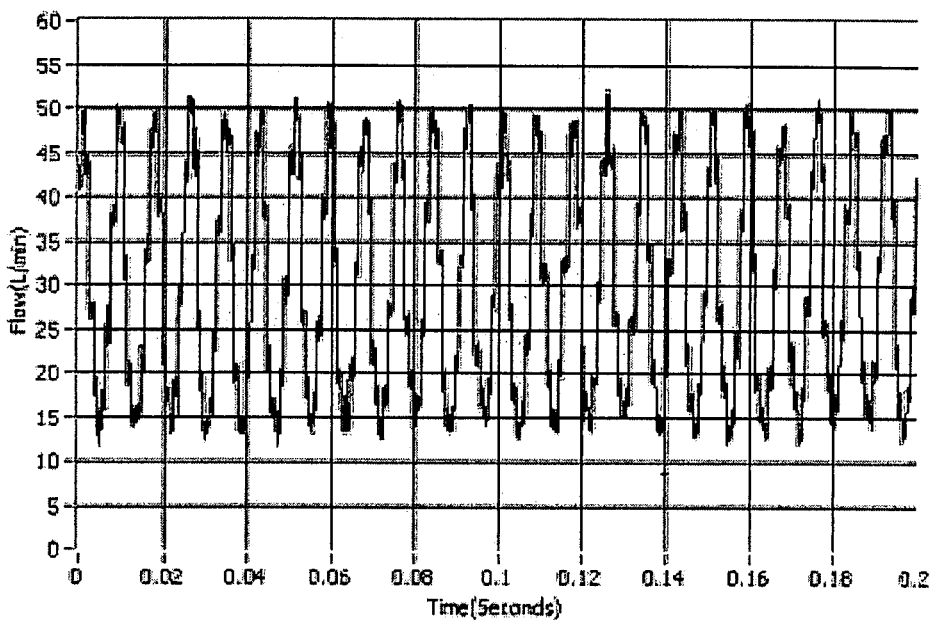
FIG. 6A is a graph depicting the output pressure of the linear pump before receiving pressure damping.
Figure 6B:
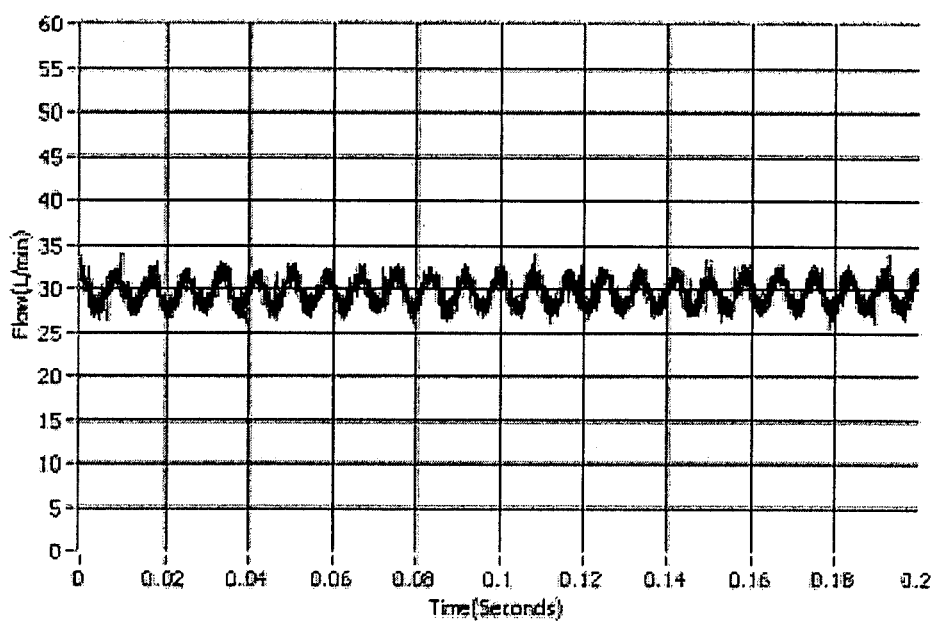
FIG. 6B is a graph of the output pressure of the linear oscillating pump after receiving pressure damping.

The linear motor driven diaphragm 258 displaces air at a rate dependent on rotor position, thus causing the flow output to oscillate over each individual stroke of the rotor. This flow oscillation resembles a sine wave of a frequency that is twice the motor's electrical frequency. Such flow rate oscillation is depicted in FIG. 6A. Therefore, before the inspiratory flow is delivered to the patient, mechanical damping is applied to the pressurized gas to remove much of the oscillatory characteristic, as depicted in FIG. 6B, making the delivered gas flow more suitable for delivery to the patient.

In an embodiment, the oscillating pump is not limited to the pump described above. Embodiments may use an oscillating pump to produce non-linear motion by a rotor. This type of oscillating pump may produce rotational rotor movement or exert an alternative force on an alternative rotor such as a spring. Further embodiments of the oscillating pump may comprise a single diaphragm.

The present invention presents the advantage of having very low average power consumption. The linear oscillating pump is efficient at producing low flow rates, but the power efficiency of the pump decreases as the flow rate increases. However, the majority of flow rates required to supplement an average breathing cycle are in the range of 0 to 40 liters per minute. These flow rates are well within the range where the pump efficiency is very high. As an example of the efficiency of an embodiment of a linear oscillating pump, a laboratory test found that for a respiratory support system driven by a flow diverting rotary pump, the rotary pump consumed an average of 84 W, while for a similarly performing respiratory support system utilizing a linear oscillating pump, the linear oscillating pump averaged only 2.9 W of power consumption over the same time period.

The electrical characteristics of an embodiment of the linear oscillating pump that may be used in an embodiment presents the advantage of a rapid response time to reach a designated target output pressure. During the acceleration of the linear oscillating pump, there are no large starting currents, low starting torque problems, nor are there any complex combinations of input voltage and electrical frequency necessary to start the motor as is often necessary in rotary devices. The linear oscillating pump takes approximately one full cycle of operation to accelerate to peak output and requires no special controls. As an example, at an electrical frequency of 60 Hz, the linear pump requires approximately 20 ms to accelerate to full flow output. This fast flow acceleration creates desirable response times for reaching target pressures. This facilitates delivering medical gas to the patient in conjunction with the patient entering the inspiratory phase of the respiration cycle.

Embodiments also present the additional benefit of added maintenance efficiency. Stock linear oscillating pumps have a long MTBF (mean time between failure) thereby running efficiently for a long time without need for replacement. This is directly related to the simple design of the linear oscillating pump and the absence of frictional moving parts. Therefore, embodiments have the additional benefit of requiring relatively low maintenance compared to current designs.

Embodiments offer the advantage of mobility, as embodiments eliminate a dependency upon pressurized drive gas tanks for a source of drive gas. The need is eliminated whether the tanks are smaller portable tanks connected directly to the ventilator or larger tanks that are connected to a room of a medical facility. This mobility makes the embodiments useful for the remote provision of medical care such as in third world countries, military field hospitals, or in rescue situations. Advanced medical care facilities to be deployed at these locations require devices that are portable as well as energy efficient as compared to existing compressor based drive gas supply systems as typically the electricity must be generated on-site.

Further embodiments exhibit the advantage of being energy efficient as the drive pump 160 replaces the inspiratory flow control valve, gas inlet valve, and a compressor type high pressure drive gas source of the prior art. The compressor type high pressure drive gas source exhibits high energy demands because it must be constantly generating pressurized gas to provide the highest flow rate needed by the ventilatory system. The inspiratory flow control valve then must continuously operate to control the flow of the drive gas from the drive gas source. Therefore, by eliminating these components of the ventilatory system of the prior art, a more energy efficient system is created.

In a further advantage of embodiments, the oscillating pump provides the advantage of being a low maintenance type of pump with a long mean time between failure (MTBF). The oscillating pump generally has few moving parts, resulting in easier maintenance and fewer parts that may fail or malfunction, requiring replacement.

Furthermore, embodiments comprise drive pumps that exhibit a fast response time, thus making the drive pumps suitable choices for replacement of both the pressurized gas source and the inspiratory flow control valve of the prior art. One example of such a drive pump is an oscillating drive pump; however, it is understood that any other pump configuration that exhibits a fast response time such to be able to match the transfer characteristics of the inspiratory flow control valve would be a suitable drive pump for use with the present invention.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Various alternatives and embodiments are contemplated as being with in the scope of the following claims, particularly pointing out and distinctly claiming the subject matter regarded as the invention.

We claim:

1. A ventilatory system for the provision of respiratory support to a patient, the ventilatory system comprising:
a linear oscillating drive pump that receives ambient air through an inlet and operates through a plurality of cycles per ventilation cycle to pressurize the ambient air to create a flow of pressurized drive gas for each ventilation cycle;
a controller in operative communication with the linear oscillating drive pump and the controller operates the linear oscillating drive pump at a motor operating frequency greater than a respiration rate of the patient and a variable voltage magnitude to control the created flow of pressurized drive gas for each ventilation cycle;

a dampening system that removes an oscillatory component from the flow of drive gas, the oscillatory component being caused by the linear oscillating drive pump;

a first inspiratory conduit connected to the drive pump such that a flow of drive gas from the drive pump is delivered to the first inspiratory conduit;

a second inspiratory conduit connected to the first inspiratory conduit such that a flow of drive gas travels from the first inspiratory conduit, into the second inspiratory conduit;

a bellows assembly comprising a bellows chamber fluidly connected to the second inspiratory conduit and a bellows in pneumatic connection with the bellows chamber; and a patient connection conduit in fluid connection with the bellows, the patient connection conduit being disposed for connection to a patient interface;

wherein the drive gas is delivered to the bellows assembly to compress the bellows, and upon compression of the bellows, the bellows delivers a medical gas to the patient connection conduit.

2. The ventilator system of claim 1 further comprising:
an expiratory conduit fluidly connected to the bellows assembly such that an expiratory flow of drive gas travels from the bellows assembly into the expiratory conduit;
an exhalation valve in the expiratory conduit, the exhalation valve being fluidly connected to the bellows assembly and the first inspiratory conduit;
wherein the exhalation valve maintains the pressure between the first inspiratory conduit and the bellows assembly in a relative equilibrium.

3. The ventilatory system of claim 2 wherein the relative equilibrium achieved by the exhalation valve is the pressure suitable to provide respiratory support to the patient during expiration.

4. The ventilatory system of claim 1 further comprising:
a pressure transducer disposed in fluid connection with the first inspiratory conduit;
wherein the controller receives a signal indicative of the pressure in the first inspiratory conduit from the pressure transducer.

5. The ventilatory system of claim 4 wherein the controller operates the linear oscillating drive pump at the motor operating frequency and a first voltage magnitude to achieve a first drive gas target pressure, the first target pressure being a pressure sufficient to provide respiratory support to the patient during inspiration.

6. The ventilatory system of claim 5 wherein the controller operates the linear oscillating drive pump at the motor operating frequency and a second voltage magnitude to achieve a second drive gas target pressure, the second drive gas target pressure being a pressure suitable to provide respiratory support to the patient during expiration.

7. The ventilatory system of claim 1 further comprising:
at least one flow transducer disposed in the patient connection conduit;
wherein the controller receives a signal indicative of the gas flow to and from the patient.

8. The ventilatory system of claim 7 wherein the controller is in operative communication with the drive pump, the controller controls the operation of the drive pump to deliver the flow of the drive gas in the first inspiratory conduit to achieve a target gas flow to the patient.

9. The ventilatory system of claim 1 further comprising:
a pressure transducer disposed in fluid connection with the first inspiratory conduit;
at least one flow transducer disposed in the patient connection conduit; and
wherein the controller receives a signal indicative of the pressure in the first inspiratory conduit from the pressure transducer, and receives a signal indicative of the gas flow to and from the patient from the at least one flow transducer.

10. The ventilatory system of claim 9 wherein the controller operates the linear oscillating drive pump at the motor operating frequency and a voltage magnitude to deliver the flow of the drive gas in the first inspiratory conduit to achieve a target gas flow to the patient.

11. The ventilatory system of claim 10 wherein the controller further signals the drive pump to achieve a target pressure, the drive gas target pressure being a pressure suitable to provide respiratory support to the patient.

12. A method of providing respiratory support to a patient via a ventilator, the method comprising the steps of:
collecting ambient air from outside of the ventilator;
operating a linear oscillating pump at a motor operating frequency and variable voltage magnitude to control a flow of the ambient air;
pressurizing the ambient air with the linear oscillating pump to create a pressurized gas flow with an oscillatory component;
removing the oscillatory component from the pressurized gas flow with a dampening system;
directing the pressurized air from the dampening system into a bellows chamber to compress a bellows filled with medical gas;
delivering the medical gas to a patient; and
operating the linear oscillating pump with a controller to deliver a target volume and a target pressure of the pressurized gas flow to the patient;
wherein the controller operates the linear oscillating pump at the motor operating frequency and a first voltage magnitude to pressurize the gas flow over a plurality of cycles of the linear oscillating pump to a first target pressure during an inspiratory phase of a breath cycle, the first target pressure being, a sufficient respiratory support pressure for the patient gas inspiration; and
wherein the controller operates the linear oscillating pump at the motor operating frequency and a second voltage magnitude to pressurize the gas flow to a second target pressure during an expiratory phase of the breath cycle, the second target pressure being lower than the first target pressure and a suitable respiratory support pressure for the patient gas expiration.

13. The method of providing respiratory support of claim 12, further comprising the steps of:
biasing the pressure in the bellows chamber to a pressure relative to the pressure in the inspiratory conduit; and
controlling the respiratory support pressure in the bellows chamber by controlling the pressure in the inspiratory conduit.

14. The method of providing respiratory support of claim 12, further comprising the steps of:
providing a flow of the ambient air to a target volume during an inspiratory phase of a breath cycle, the target volume being a suitable respiratory support volume; and
pressurizing the ambient air to a target pressure during an expiratory phase of the breath cycle, the target pressure being a suitable respiratory support pressure for patient gas expiration.

15. The method of providing respiratory support of claim 12, further comprising the step of sonically isolating the linear oscillating pump.

16. A mobile ventilatory system for providing respiratory support to a patient, the respiratory support including the provision of PEEP support, the system comprising:
   a linear oscillating pump having an inlet to receive ambient air and operating at a motor operating frequency greater than a respiration rate of the patient;
   a controller in operative communication with the oscillating pump to selectively control a voltage magnitude to the linear oscillating pump to operate the linear oscillating pump to pressurize the ambient air to provide a flow of drive gas, the flow of drive gas having an oscillatory component from the linear oscillating pump;
   a dampening system that receives the flow of drive gas from the linear oscillating pump and attenuates the oscillatory component from the flow of drive gas;
   an inspiratory conduit connected to the dampening system to receive the flow of drive gas from the dampening system;
   a bellows assembly connected to the inspiratory conduit, the bellows assembly including a bellows in pneumatic connection with the inspiratory conduit such that the bellows is compressed by the flow of drive gas; and
   a patient connection conduit in fluid connection with the bellows and disposed for connection to the patient, wherein the controller operates the linear oscillating pump with a first voltage magnitude to provide a flow of drive gas to achieve a first drive gas target pressure to provide respiratory support to the patient and the controller operates the linear oscillating pump with a second voltage magnitude to provide a flow of drive gas to achieve a second drive gas target pressure to provide PEEP support to the patient, wherein the oscillating pump, and controller are in a single mobile unit.

17. The mobile ventilatory system of claim 16 further comprising an exhalation valve fluidly connected to the bellows chamber and the inspiratory conduit such that the exhalation valve releases the pressure from the bellows chamber to maintain the pressure in the bellows chamber relative to the pressure in the inspiratory conduit.

18. The mobile ventilatory system of claim 16 wherein the linear oscillating pump comprises opposed first and second diaphragms, such that each diaphragm is operated by the linear oscillating pump to pressurize ambient air in opposed operational cycles and the dampening system receives the flow of drive gas from both the first and second diaphragms.

* * * * *